United States Patent [19]

Repke

[11] 4,125,114

[45] Nov. 14, 1978

[54] DISPOSABLE NURSING PAD

[75] Inventor: Virginia L. Repke, Oak Forest, Ill.

[73] Assignee: Johnson & Johnson, New Brunswick, N.J.

[21] Appl. No.: 801,827

[22] Filed: May 31, 1977

Related U.S. Application Data

[63] Continuation of Ser. No. 653,982, Jan. 30, 1976, abandoned.

[51] Int. Cl.² .............................................. A61M 1/00
[52] U.S. Cl. ................................................... 128/280
[58] Field of Search .............. 128/280, 290 R, 290 W, 128/284, 287

[56] References Cited

U.S. PATENT DOCUMENTS

| | | | |
|---|---|---|---|
| 2,896,623 | 7/1959 | Fitzgerald | 128/280 |
| 3,356,090 | 12/1967 | Plantinga et al. | 128/280 |
| 3,663,348 | 5/1972 | Liloia et al. | 128/284 X |
| 3,886,942 | 6/1975 | Bernardin | 128/290 R |
| 4,014,341 | 3/1977 | Karami | 128/290 R X |

FOREIGN PATENT DOCUMENTS 1,143,146  2/1969  United Kingdom ..................... 128/280

Primary Examiner—Robert W. Michell
Assistant Examiner—Michael H. Thaler

[57] ABSTRACT

A disposable nursing pad is provided which comprises a dished or cup-shaped body constructed of a plurality of substantially coextensive layers and having an inner concave surface and an outer convex surface. The inner concave surface is adapted to substantially conform to a human breast. A moisture impervious material is provided at the outer convex surface, an absorbent material is disposed inwardly thereof and a moisture permeable but non-wettable material defines the inner concave surface. The several layers of the pad are secured together by sewing or similar securement means.

5 Claims, 4 Drawing Figures

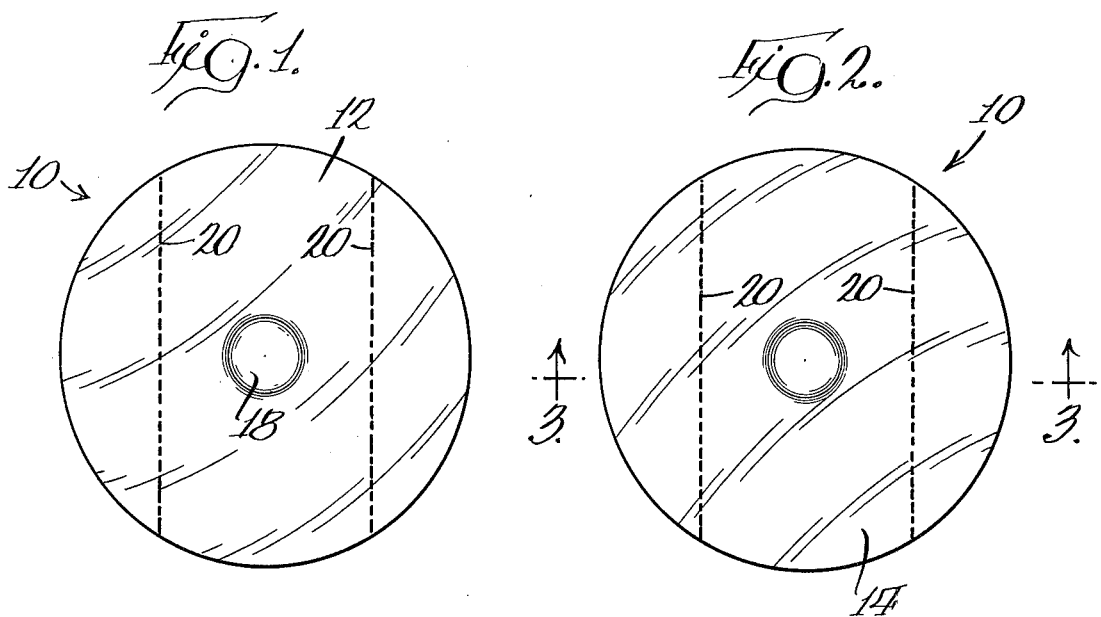
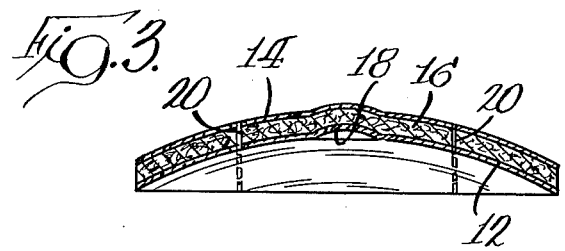
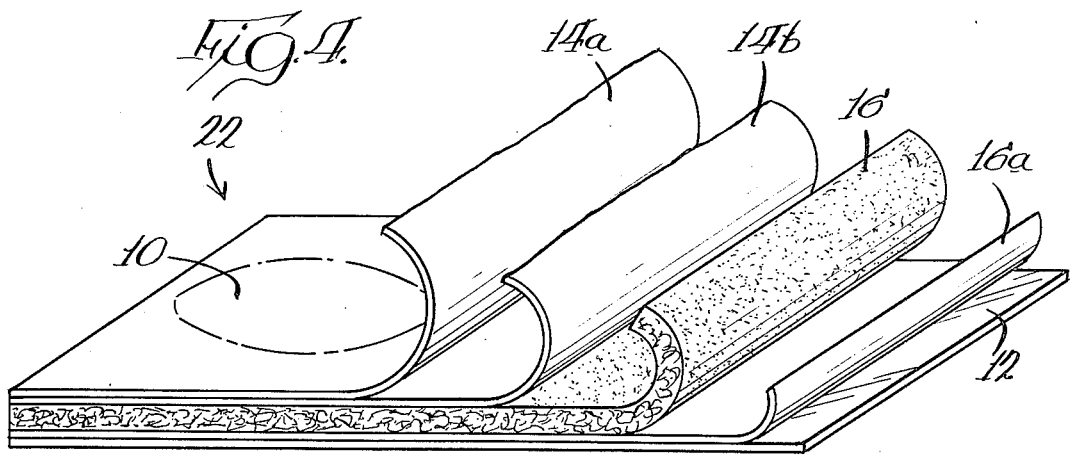

DISPOSABLE NURSING PAD

This is a continuation of application Ser. No. 653,982, filed Jan. 30, 1976, now abandoned.

BACKGROUND OF THE INVENTION

Disposable nursing pads are widely used by nursing mothers to prevent strike-through of milk onto their clothing. Nursing pads generally comprise several tissue layers stitched together with an absorbent layer to absorb fluid. Typical such nursing pads are shown in U.S. Pat. No. 2,896,623 and 2,891,544. However, the presently available nursing pads suffer from a number of disadvantages. One of the disadvantages of the prior art pads is the problem of strike-through in the stitching areas. Another problem is that of the undesirable soggy feel to the mother after she has worn the pad for a period of time. Yet another problem is that the nursing pad sometimes disintegrates while being used. Thus, there is a need for an improved nursing pad which minimizes the strike-through problem, and which enhances comfort of the nursing mother while in use. The present invention provides such a nursing pad.

SUMMARY OF THE INVENTION

The present invention provides an improved, disposable nursing pad which is generally dished or cup-shaped and is constructed of a plurality of substantially coextensive layers having different characteristics: a facing layer of moisture permeable but non-wettable material; an absorbent layer and a backing layer of moisture impervious material.

The nursing pad of this invention has a number of advantages over currently available nursing pads. The facing layer provides a dry surface next to the mother's skin which is far preferable to the cold, soggy feel presently encountered by nursing pad users and thus enhances the comfort of the nursing mother. The nursing pad further prevents strike-through of milk onto the mother's clothing which is common and distressing with currently available nursing pads. The moisture impervious backing layer prevents the problem of strike-through. Furthermore, the nursing pad of this invention is not as subject to disintegration when wet as are the currently available pads. Thus, the present invention provides a nursing pad which is aesthetically superior to currently available nursing pads and which provides greater comfort to the mother.

The nursing pad of this invention is generally dished or cup-shaped so as to conform to the contour of the mother's breast. The facing layer defines an inner concave surface and the backing layer defines an outer convex surface which is adapted to be received within a brassiere. The absorbent layer is disposed between the facing layer and the backing layer. The moisture permeable, non-wettable facing layer allows fluid to pass through it but remains relatively dry. The absorbent layer wicks the fluid away from the facing layer. The fluid-impervious layer prevents the fluid wicked from the facing layer and retained by the absorbent layer from striking through onto the mother's clothing.

Several different types of facing materials may be used for the facing layer. For example, the facing layer may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing materials suitable for use in this invention can have fabric weights in the range of about 0.2 to about 2.5 oz./yd.$^2$ and densities of less than 0.25 g./cc., generally in the range between 0.05 and 0.2 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

The facing layer may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occuring fibers, synthetic fibers, or blends thereof. Typical facing sheets made of a polyester type material can have a weight of about 0.5 to 1.0 oz./yd.

In addition, the facing layer can be formed of a non-apertured material, such as a non-woven isotropic web, or the like. In all of the aforementioned facing materials, the material should be relatively hydrophobic so as to retard wicking within the facing layer. Also suitable are porous polymeric sheet materials such as polyolefin webs, e.g., polyethylene webs, having a fibrous or fiber-like surface, and the like.

As is apparent from the above discussion, a number of materials are suitable for use as the facing layer. However, it is presently preferred to use a thermoplastic, spun bonded, fibrous non-woven fabric produced from continuous filaments of polypropylene sold under the trade name Fibretex ® by Crown Zellerbach Corporation. The Fibretex ® fabric is 100 percent polypropylene. It has high permeability, is non-absorbent, has high tear strength, good drape and hand, is heat sealable and has good stitch strength as well as resiliency. The weight of the fabric is generally from about 0.5 to about 2.5 oz./yd.$_2$ and the density is about 0.109 to 0.184 gms./cc. The Fibretex ® fabric, being heat sealable, can be bonded directly the the contiguous surface of the absorbent layer during the manufacturing process.

Turning now to the absorbent layer, while a number of suitable materials can be utilized, the absorbent layer preferably is constructed of laminated tissue wadding. The facing layer is heat bonded to a contiguous face of the absorbent layer.

A suitable backing layer material can be a moisture impervious tissue, or a liquid impermeable polyolefin web such as an opaque polyethylene web about 0.001 inch thick, a polyethylene terephthalate web having a thickness of about 0.0005 inch, and the like.

The nursing pad is preferably held together by two spaced apart parallel rows of stitching which generally divide the surface of the nursing pad into three areas. The central area is the widest area and can have a nipple receiving depression stamped therein during manufacture.

In the manufacture of the improved nursing pad of this invention, a web which comprises the various plies or layers is fed through a die set which stamps out the individual nursing pads. The nipple receiving depression can be stamped at the same time the nursing pad is cut, and the facing layer can simultaneously be bonded to the thin absorbent layer. The cut-out pads are then fed through automatic sewing equipment whih permits two or more sewing heads to function concurrently, or alternatively, the stitching can be accomplished prior to the cutting operation.

BRIEF DESCRIPTION OF THE DRAWINGS

In the drawings:

FIG. 1 is a bottom view of the nursing pad of this invention;

FIG. 2 is a top view of the nursing pad of this invention;

FIG. 3 is a cross-sectional view taken along plane 3—3 in FIG. 2;

FIG. 4 is a perspective fragmentary view of the layered material from which the nursing pads of this invention are produced.

DETAILED DESCRIPTION OF THE PREFERRED EMBODIMENT

Referring now to the drawings, the present invention provides a disposable nursing pad 10 which is generally dished or cup-shaped so as to conform to the contour of the mother's breast and is constructed of a plurality of substantially co-extensive layers having different characteristics: a facing layer 12 of moisture permeable but non-wettable material which defines an inner concave surface of nursing pad 10 and is adapted to contact the breast, a backing layer 14 of moisture impervious material adapted to be received within a brassiere and an absorbent layer 16 disposed between facing layer 12 and backing layer 14. The moisture permeable, non-wettable facing layer 12 allows fluid to pass through it but remains relatively dry. Absorbent layer 16 wicks the fluid away from the facing layer. Fluid impervious backing layer 14 prevents the fluid wicked from facing layer 12 and retained by absorbent layer 16 from striking through onto the mother's clothing. Nipple depression 18 is stamped into the nursing pad 10 during construction and nusing pad 10 is preferably secured together by two spaced apart, parallel rows of stitching 20.

It is to be understood that each of the layers may be constructed of one or more plies of a suitable material. Turning to FIG. 4, in the preferred embodiment, nursing pad 10 is constructed of non-woven tissue materials having differing properties. While facing layer 12 can be one of a number of suitable moisture permeable, but non-wettable materials which will keep the surface of nursing pad 10 relatively dry and comfortable to the mother, the preferred material is a porous polymeric sheet material such as polyalkylene webs having a fibrous surface. The presently preferred material is a spun-bonded non-woven fabric produced from continuous filaments of a polyolefin such as polypropylene. A particularly suitable fabric is commercially available under the trade name Fibretex ® from Crown Zellerbach Corporation. The Fibretex ® fabric is 100 percent polypropylene. It has high permeability, is non-absorbent, has high tear strength, is resistant to rot and mildew, has good wet strength, good drape and hand, is heat sealable and has good stitch strength as well as resiliency. The fabric weight is generally from about 0.5 to about 2.5 oz./yd.$^2$ and has a density of 0.109 to 0.184 gms./cc. The Fibretex ® fabric, being heat sealable, can be bonded to the contiguous surface of the absorbent layer 6 during the manufacturing process. In one preferred embodiment, facing layer 12 consisted of one ply of Fibretex ® fabric having a fabric weight of 0.5 oz./yd.$^2$ Absorbent layer 16 is preferably a multi-ply tissue layer and, in one preferred embodiment consisted of 18 plies of conventional absorbent tissue such as that sold by Cel-Fibe Company under the designation Absorbent Cel-Fibe Code (2001).

Backing layer 14 is preferably a water repellent tissue material. In the preferred embodiment, backing layer 14 has an outer ply 14a which contacts the brassiere and an inner ply 14b which is contiguous with one face of absorbent layer 16. Outer ply 14a is preferably one ply of Pink Masslinn tissue manufactured by Chicopee Manufacturing Co. Pink Masslinn tissue is a non-woven fabric which is treated to be moisture repellent. Inner ply 14b is preferably a single ply of Repellent Cel-Fibe Code (4402) moisture repellent tissue manufactured by Cel-Fibe Company.

In the manufacture of the improved nursing pad 10 of this invention, a web 22 which comprises the various plies or layers 12, 16a, 16, 14b and 14a respectively, as shown in FIG. 5, is fed through a die set which stamps out the individual nursing pads 10, shown in phantom in FIG. 5. The nipple receiving depression 18 can be stamped at the same time nursing pad 10 is cut and the facing layer 12 can be simultaneously bonded to absorbent layer 16a. The cut-out pads are then fed through automatic sewing equipment which permits two or more sewing heads to function concurrently.

It will be understood by those skilled in the art that variations and modifications of the specific embodiments described above may be employed without departing from the scope of the invention as defined in the appended claims.

I claim:

1. A disposable nursing pad in the form of a dished body, having a smooth and continuous inner concave surface adapted to substantially conform to the contour of a human breast and an outer convex surface adapted to be received within a brassiere which comprises a moisture-permeable hydrophobic, spun-bonded, non-woven, thermoplastic, fibrous facing layer defining said inner concave surface, said facing layer having a fabric weight of about 0.2 to about 2.5 oz./yd.$^2$, an absorbent layer substantially coextensive with said facing layer and having one surface thereof in contiguous engagement with one surface of said facing layer, securement means consisting of a heat bond between said contiguous surfaces throughout their area of engagement, a moisture-impermeable backing layer overlying said absorbent layer and substantially coextensive with said absorbent layer and said facing layer, and further securement means for binding said facing, said absorbent layer, and said backing layer to form a unitary pad, said further securement means being in the form of substantially parallel lines of stitching joining said layers together, whereby said nursing pad is resistant to disintegration when wet.

2. The disposable nursing pad of claim 1 wherein said facing layer has a fabric weight of about 0.5 to about 1 oz./yd.$^2$.

3. The disposable nursing pad of claim 1 wherein the density of said facing layer is about 0.05 to about 0.25 grams per cubic centimeter.

4. The disposable nursing pad of claim 1 wherein the material of said facing layer is a spun bonded, nonwoven fabric produced from continuous filaments of polypropylene.

5. The disposable nursing pad of claim 1 wherein the material of said facing layer is a polyolefin web having a fibrous surface.

* * * * *